United States Patent [19]

Fuisz

[11] Patent Number: 4,855,326
[45] Date of Patent: Aug. 8, 1989

[54] RAPIDLY DISSOLUBLE MEDICINAL DOSAGE UNIT AND METHOD OF MANUFACTURE

[75] Inventor: Richard C. Fuisz, Bethlehem, Pa.

[73] Assignee: Fuisz Pharmaceutical Ltd., Washington, D.C.

[21] Appl. No.: 169,838

[22] Filed: Mar. 18, 1988

Related U.S. Application Data

[63] Continuation-in-part of Ser. No. 40,371, Apr. 20, 1987, abandoned.

[51] Int. Cl.⁴ .................... A61K 9/00; A61K 9/70
[52] U.S. Cl. .................... 514/777; 514/781; 424/439; 424/443; 206/569
[58] Field of Search .............. 514/772, 777, 781; 424/400, 439, 440, 445; 425/9; 426/658, 660, 517; 206/569

[56] References Cited

U.S. PATENT DOCUMENTS

| | | | |
|---|---|---|---|
| 2,826,169 | 3/1958 | LeVeen | 424/59 |
| 3,019,745 | 2/1962 | DuBois et al. | 425/9 |
| 3,036,532 | 5/1962 | Bowe | 425/9 |
| 3,070,045 | 12/1962 | Bowe | 425/9 |
| 3,073,262 | 1/1963 | Bowe | 425/9 |
| 3,324,061 | 6/1967 | Tanguary et al. | 264/177.13 |
| 3,557,717 | 1/1971 | Chivers | 426/517 |
| 3,595,675 | 7/1971 | Ash et al. | 426/658 |
| 3,615,671 | 10/1971 | Groesbed et al. | 426/660 |
| 3,723,134 | 3/1973 | Chivers | 426/660 |
| 3,856,443 | 12/1974 | Salvi | 425/9 |
| 3,875,300 | 4/1975 | Homm et al. | 424/28 |
| 3,930,043 | 12/1975 | Warning et al. | 426/517 |
| 3,967,623 | 7/1976 | Butterworth et al. | 604/390 |
| 4,136,145 | 1/1979 | Fuchs et al. | 424/443 |
| 4,492,685 | 1/1985 | Keith et al. | 424/443 |
| 4,496,592 | 1/1985 | Kuwahara et al. | 426/5 |
| 4,526,525 | 7/1985 | Obo et al. | 425/9 |
| 4,585,797 | 4/1986 | Croca | 424/20 |

*Primary Examiner*—John Kight
*Assistant Examiner*—Nathan M. Nutter
*Attorney, Agent, or Firm*—Brooks Haidt Haffner & Delahunty

[57] ABSTRACT

A melt spinnable carrier agent such as sugar is combined with a medicament then converted into fiber form by melt spinning with "cotton candy" fabricating equipment. The as-spun product is converted to compacted individual dosage units. For certain medicaments a binding agent is added to the carrier agent. Examples are presented for oral administration, topical application, systemic and non-systemic, intravenous and intramuscular infusion via multicameral containers. All applications utilize the extraordinarily rapid entry into solution upon contact with a solvent.

59 Claims, No Drawings

RAPIDLY DISSOLUBLE MEDICINAL DOSAGE UNIT AND METHOD OF MANUFACTURE

BACKGROUND OF THE INVENTION

This application is a continuation-in-part of application Ser. No. 040,371, filed Apr. 20, 1987 and now abandoned.

The present invention relates to a medicinal dosage unit, e.g., a tablet or the like, and to a method of producing the same. More particularly, it relates to a non-liquid dosage unit that is rapidly dissoluble for use in administering a medicinal substance either orally, topically or by infusion.

It is well known that a substance placed in the oral cavity of an animal, if absorbable by body tissue, is absorbed much more effectively than if the same substance were introduced directly into the stomach or digestive tract. Therefore, many medicinal substances are administered either lingually, sublingually or buccally. However, some medicinal substances, while for the sake of effectiveness and economy would best be administered lingually, sublingually or buccally, cannot be so administered because of an undesirable taste attribute and/or a slowness to dissolve.

In pediatric practice, when oral administration is desired, there exists the additional problem of insuring that the medication remains in the mouth and is swallowed and not expelled even if there is no antagonistic taste characteristic. In animal husbandry much the same problem exists regardless of taste.

Consequently, there is a great need for some form by which medication can be administered orally and be rapidly dissolved and absorbed with sufficient speed as to avoid significantly the foregoing problems. Others have recognized and worked on the problem. In Gregory et al. U.S. Pat. No. 4,371,516 issued Feb. 1, 1983, there is described a shaped article or pharmaceutical dosage form carrying a pharmaceutical in which the article comprises an open matrix network of carrier material which is prepared by subliming solvent from a composition comprising the pharmaceutical and a solution of the carrier material in a solvent, e.g., a hydrolyzed gelatin solution. According to the patent some embodiments dissolve in the saliva of the mouth in one or two seconds. The patent describes the open matrix network as being similar in structure to a solid foam. Unfortunately, the Gregory et al. product is still too slow to dissolve for many purposes and has other drawbacks.

Certain drugs in solid or tablet form or the like are intended to be ingested and are therefore taken with water or other liquid. Among such drugs, the therapeutic value is a function of the speed with which they dissolve. While some are deliberately designed with a delayed action, others should dissolve as rapidly as possible. Ideally, the medicament should dissolve so rapidly that when taken with a liquid it is swallowed practically as a solution.

There are various forms for administering a medicament topically. Salves and ointments immediately come to mind. However, there are various situations where the medicament is required only when the dermal area becomes moist such as when a wound bleeds or produces a secretion. Also, release of the active agent from a salve or ointment is comparatively slow whereas there are occasions when rapid delivery is desirable. Moreover, salves and ointments tend to be messy, the major constituent is the vehicle and not the active agent, and they are difficult if not impossible to spread uniformly over the skin. The amount of material and therefore the concentration of medicament is greatest at the point of direct application, and then, as with a snowplow, gradually thins out as it is spread from the point of application over the surface of the skin.

In another area, packaging of generally unstable dry medicaments for production of intravenous solutions currently involves use of a costly production technique whereby the medicament is lyophilized using a freeze drying procedure. A bicameral container is then employed to isolate the dry freeze dried pharmaceutical from a solvent such as distilled water or the like, until immediately prior to infusion. Immediate sediment-free dissolution in the solvent is required.

SUMMARY OF THE PRESENT INVENTION

It is an object of the present invention to provide a rapidly dissoluble medicinal dosage unit that is more rapidly dissolved and absorbed and is more palatable than anything known heretofore.

It is another object of the present invention to provide a rapidly dissoluble medicinal dosage unit of controllable potency that is relatively inexpensive to produce.

Another object is to provide a dry medicinal form that is less expensive to manufacture than freeze dried product yet dissolves at least as rapidly if not more rapidly than lyophilized material.

Other objects will occur to those skilled in the subject art after reading the following detailed description.

In accordance with one aspect of the present invention there is provided a spun fibrous pharmaceutical composition comprising a mass of spun fibers of a readily water-soluble material capable of being spun into fibers and a medicament distributed on or incorporated in said fibrous mass.

In accordance with another aspect of the present invention there is provided a system for topical transdermal delivery of a medicament comprising a wafer containing a mass of fibers, and means for securing said wafer in contact with a dermal area to be treated, said mass of fibers comprising a soluble fiber forming ingredient and a medicament where at least said fiber forming ingredient has been spun into fibers, and in said fiber form said ingredient has a solubility characteristic corresponding to that of spun sugar fibers in water.

In accordance with a further aspect of the present invention a bicameral container for intravenous administration is provided with a first compartment containing a pharmaceutically acceptable solvent, and a second compartment containing a spun fibrous pharmaceutical composition comprising a mass of spun fibers of a readily water-soluble material capable of being spun into fibers and a medicament distributed on or incorporated in said fibrous mass.

Yet, in accordance with another aspect of the present invention there is provided a method for preparing a rapidly dissoluble medicinal dosage unit for administering medication orally, comprising in combination the steps of combining a medicament with a melt spinnable compatible carrier agent to provide an intermediate product, and producing a mass of medicament bearing fibers by melt spinning said intermediate product.

The invention will be better understood after reading the following detailed description of the presently preferred embodiments thereof.

DETAILED DESCRIPTION OF THE PRESENTLY PREFERRED EMBODIMENTS

The spun sugar fiber confection of sucrose, commonly referred to as cotton candy, is well known to children and most adults. Also, it should be obvious to all who have eaten cotton candy that the sucrose sugar literally melts in the mouth and seems very quickly to disappear to nothing. In its spun form the sugar is very fragile. However, the sugar fibers can be compacted to form a sheet-like body that can be handled more readily. Two patents describe methods for producing compacted confections from spun sugar, namely Warning et al. U.S. Pat. No. 3,930,043 and Oiso et al. U.S. Pat. No. 4,526,525.

In U.S. Pat. No. 4,496,592 of Kuwahara et al. a chewing gum is described that is produced in the form of composite fibers by fiberizing a sugar and/or a candy and a chewing gum base or composition through a fiberizing section, such as a rotating cylinder, of a candy floss making machine.

Of the foregoing patents, none considers or suggests the possibility of using any form of fibrous sugar or cotton candy as a carrier for a medicament, a pharmaceutical component.

With that as background, it has been discovered that many pharmaceutical compounds useful as medicaments can, in fact, be combined with a spinnable readily dissoluble material, such as sugar, in such manner that the resultant composition can still be spun into fiber form by melt spinning and without deteriorating the medicament or reducing its effectiveness. Generally speaking, the particular sugar or other material used as a carrier agent should have a melting point that is a safe distance below that temperature at which the medicament might decompose or otherwise break down, but not necessarily below the melting point of the medicament. Subject to that requirement, any material, such as sugar or a sugar-like substance that can be melt spun to produce a fibrous structure which substance dissolves rapidly in water, the saliva of the mouth, or other sera, is non-toxic, and is compatible with the particular medicament, is suitable in the practice of the present invention.

From a dosage standpoint, it has also been discovered that the method to be described is able to produce with acceptable reliability consistent and uniform distribution of the medicament throughout the carrier agent. This is essential for medicinal use where the quantity of effective medicament in each dosage unit should be known or ascertainable.

The present invention can best be explained by considering a series of examples. First, a pediatric formulation was prepared using acetaminophen (abbreviated APAP). The objective was to provide a product containing 60 mg acetaminophen per gram of product. A thick slurry of acetaminophen was prepared consisting of 60-70% w/v acetaminophen in isopropyl alcohol. A measured quantity of common granular sugar was added to the slurry and the sugar granules were coated uniformly with the slurry. The coated sugar granules were then dried for 3-4 hours at a temperature that varied between 45° C. and 65° C. (113° F.-149° F.), the target control temperature being about 50° C. (122° F.).

Next, using conventional "cotton candy" spinning equipment, operating at a melt temperature that ranged between 90° C. and 130° C. (194° F.-266° F.), the coated granules were converted to spun fiber form having the consistency and physical appearance of cotton candy. In order to determine the uniformity of the resultant product, three different portions of the fibrous product were sampled from different sections of the batch and each portion was analyzed to determine the acetaminophen content. The results are in Table I.

TABLE I

| Sample No. | mg of Acetaminophen per gram of fibrous product | Percent Acetaminophen per dosage unit |
|---|---|---|
| 1 | 54.6 mg | 91.0% |
| 2 | 57.0 mg | 95.0% |
| 3 | 52.2 mg | 87.0% |

The results indicate that the medicament has been uniformly distributed. The samples were also tested for taste and were found to be slightly bitter but in the acceptable range.

Next, a formulation for animal husbandry was attempted using diethylcarbamazine citrate (abbreviated DCM citrate) for which the target dosage was 200 mg per gram of fibrous product. This medicament is useful as an anthelmintic.

A thick slurry of the medicament was prepared with 60% w/v of diethylcarbamazine citrate in isopropyl alcohol. Sugar granules were added and coated with the slurry and then dried for 3-4 hours at a temperature that varied between 45° C. and 65° C. (113° F.-149° F.), the target control temperature being about 50° C. (122° F.). Upon drying it was observed that the medicament did not adhere effectively to the sugar granules which could result in lack of uniformity in the final product.

The isopropyl alcohol (abbreviated (IPA) was then replaced with purified water but it was impossible to obtain completely dry granules.

Finally, good adhesion was obtained by adding a promoter of adhesion to the isopropyl alcohol before mixing with the drug. Specifically, a 2-3% solution by weight of polyvinylpyrrolidone (abbreviated PVP) in isopropyl alcohol was prepared, and this solution was used to prepare a thick slurry with diethylcarbamazine citrate, again incorporating about 60% w/v of the medicament in solution. A measured quantity of common granular sugar was then coated with the slurry and dried for 1-3 hours at a temperature similar to that used with the prior examples. This product was then spun in the "cotton candy" apparatus to produce an end product from which samples were taken and assayed using spectrophotometric procedures. The results were presented in Table II.

TABLE II

| Sample No. | mg of diethylcarbamazine citrate per gram of fibrous product | Percent of diethylcarbamazine citrate per dosage unit |
|---|---|---|
| 1 | 174 mg | 87% |
| 2 | 166 mg | 83% |
| 3 | 188 mg | 94% |

While PVP is specifically mentioned as an adhesion promoter, it is intended merely as an example of a non-toxic, compatible, pharmaceutically acceptable, ingestible film former.

The results of additional tests to produce a number of medicaments (drugs) in fiber form are tabulated below in Table III. In the column headed "DRUG", the letters identify the drug in accordance with the following list while the numbers indicate the weight in grams.

A = acetaminophen (APAP)
C = chlorpheniramine maleate (CPM)
D = diethylcarbamazine citrate (DCM)
M = metoclopramide hydrochloride
P = phenylpropanolamine (PPA)
Z = mucopolysaccharide In the column headed "SUGAR" the numbers indicate the weight in grams of common table sugar, i.e., granulated sucrose, unless noted otherwise. Unless otherwise noted, the "SOLVENT" was isopropyl alcohol (IPA) in approximately the volume indicated in milliliters. Drying temperatures are approximate and given in degrees Celsius, and unless indicated otherwise, was accomplished at approximately 40° C. for ½ hour. Unless a different procedure is mentioned under "REMARK", the drug was dissolved in the solvent to produce a slurry to which the sugar was added and coated uniformly. The coated sugar was then dried and spun into fibers.

while avoiding fracturing of the fibers or loss of the discrete fibrous identity. However, it will become apparent from the ensuing description that there will be occasions when a lesser degree of compaction or even no compaction is desirable. When compaction is employed, it preferably is performed to produce a body with an enclosed volume that is at least 30% less than the as-spun enclosed volume.

Various procedures can be followed to produce discrete dosage units. It is assumed that the medicament is uniformly distributed on or incorporated in the fibrous mass. A measured weight or volume of the as-spun product can be compacted as discrete units and sealed within a moisture proof package or wrapper. Alternatively, the as-spun product can be compacted on a continuous basis to produce a sheet or web which is subsequently subdivided to produce the individual units. These units can be packaged, preferably individually, using any known and appropriate technique that will exclude moisture since, depending upon the sugar, the fiber products have varying degrees of stability under normal humidity conditions.

TABLE III

| TEST NO. | DRUG (gms) | SUGAR (gms) | SOLVENT (ml) | DRYING | REMARK |
|---|---|---|---|---|---|
| 1 | A-8 | 100 | 12 | | |
| 2 | D-10 | 50 | 15 | | |
| 3 | D-10 | 50 | H₂O - 5 | 45–60° C. | Never obtained dry mass |
| 4 | D-10 | 50 | 0.4 g PVP in 15 ml IPA | 40–45° C. for ½ hr. | |
| 5 | A-5 | 50 | 12 | | |
| 6 | Coated A-5 | 50 | 12 | | |
| 7 | A-5 | 50 | IPA-12 + 4 drops of peppermint oil | | |
| 8 | D-10 | 50 | 15 | | |
| 9 | A-5 micronized | 50 | 15 | | |
| 10 | M-1.182 | 100 | 10 | | |
| 11 | A-8 | 100 | 12 | | |
| 12 | C-0.4 | 100 | 10 | | |
| 13 | P-3.75 + C-0.6 | 295.65 | 20 | | |
| 14 | C-0.6 | 299.4 | 20 | | |
| 15 | Z-5 | 95 | | | Mixed drug and sugar and spun fibers |
| 16 | C-0.4 | 99.6 | 10 | | |

The spinning process for producing "cotton candy" is a melt extrusion process in which the stock material is melted and forced through spinnerettes. The conventional equipment uses a rotating spinning head surrounded by a bowl into which the fibers are spun. Using a medicated sugar formulation, medicated fibers are obtained. In order to convert the cottonlike mass to a form that can be packaged and handled, the aspun product generally must be compacted to produce a compact body being careful not to squeeze too much. It is important that the final dosage form retains its fibrous character so that it will dissolve rapidly in the saliva of the mouth or other solvent. At present, it is believed desirable for "tablet" production to reduce the initial spun volume by approximately two thirds or until the threshold is reached beyond which the fibers would fracture or coalesce. Preferably, the material is compacted as much as possible to produce a wafer-like structure Compaction of the fibrous mass can be accomplished before or during packaging or both. Partial compaction can be achieved between rollers or the like, with the resultant fibrous web entering between layers of packaging film. Then platens or the like can be applied to seal the individual units with squeezing of the film layers further compacting the fibers. The units can be severed either before, after or during the sealing step. Ultrasonic devices can be used to accomplish sealing and severing, or die cutters can be employed. It is contemplated that any suitable packaging technology can be employed so long as the packaging material excludes moisture and does not compress the fibrous mass to the point of destroying its fibrous structure.

At present, it is preferred to use a foil laminate material and allow the fiber product to cool to ambient temperature under controlled dry conditions before encapsulating in a foil laminate pouch. It has been found that attempts to seal the fiber product while still warm were unsatisfactory because of the tendency for moisture in the atmosphere to condense on the cool foil and remain trapped within the pouch to cause deterioration of the fiber structure. An acceptable packaging laminate is a mylar-foil laminate.

Any material capable of being spun into fibers and readily dissoluble in water may be used as the carrier agent. Presently preferred materials are sugars such as sucrose, fructose, dextrose, mannitol, sorbitol, flucose, lactose and maltose; and water soluble cellulosic materials such as methyl cellulose, ethyl cellulose, hydroxy methyl or ethyl cellulose and alkali metal salts of carboxy methyl cellulose. Particularly useful, for example, is a mixture of sucrose and lactose, in which the useful ratio of sucrose to lactose may vary from 90:10 to 50:50. Lactose is a preferred sugar by reason of its relative stability under humid conditions. However, lactose is less sweet than sucrose and it is generally desirable to combine it with a sweetener.

Additives, such as coloring agents, flavoring agents, artificial sweeteners, having acceptable food and drug approval, and which are compatible with the carrier agent and medicament, can be included in the product that is melt extruded. For example, lactose has been spun successfully after having been combined with saccharin and aspartane.

While the components discussed herein have been produced by coating the granules of the carrier agent with the medicament, it is contemplated that the medicament can be distributed within the carrier by co-crystallization from a solution containing both the carrier agent and the medicament, or by any other known technique.

There are a number of drugs presently available which are given intravenously but which are unstable for storage in a liquid state. In order to package and supply such drugs in convenient form, bicameral or multicameral containers are used with the dry drug constituent in one compartment and a solvent such as distilled water or saline solution in another compartment isolated from the first compartment until, immediately prior to infusion, an intercompartmental seal is pierced or broken. For obvious reasons the FDA has stringent guidelines as to particulate residue that might remain undissolved at time of infusion and create a risk if such residue were to enter the veins or muscle mass of a patient. Consequently, current practice is to subject the drug to an expensive and difficult freeze drying or lyophilization process which produces particles with sponge-like pores fostering rapid entry into solution. Typical drugs presently packaged in this fashion are corticosteroids such as methylprednisolone sodium succinate sold under the "Solu-Medrol" brand name by The Upjohn Company, antibiotics such as cefazolin sodium sold under the "Kefzol" brand name by Eli Lilly and Company, vitamins such as B vitamins sold under the "Solu-B" brand name by The Upjohn Company, and numerous drug/parenteral-fluid preparations packaged by Baxter Travenol.

It has been discovered, however, that producing the drugs in fiber form as described in this application results in a dry quantum of the drug that is easier to manufacture, much less costly to produce, and that functions in the bicameral or multicameral environment as well if not better than lyophilized material. Since the fibrous product is hermetically sealed in a glass vial or other container until use, it has adequate shelf life.

In order to test this concept four glass vials of methylprednisolone sodium succinate produced by Abbott Pharmaceuticals, Inc. under its "A-Methapred" trademark, and containing 125 mg/vial, were emptied and the solid contents (the liquid diluent was discarded) were mixed with 20 grams of crystalline Lactose USP (hydrous), and granulated with isopropanol. The resulting material was dried on paper toweling and spun using commercial cotton candy apparatus at the high heat setting. A quantity of the resultant floss was rolled into a mass weighing approximately 0.5 gram and capable of being placed in the Abbott Pharmaceutical, Inc. vial. Thus, the dosage contained 0.0125 gm of medicament. This test obviously only establishes the feasibility of the concept and is not intended to produce an injectable product. For commercial production the compounding should be accomplished in a clean-room environment with the use of highly refined sugar and drug. In order to duplciate the original dosage level, either 5 grams of fiber material would have to be included in the vial or 10 times the concentration of drug would have to be used when compounding. It should be understood that in all cases appropriate steps must be taken to establish and insure sterility of the product.

Additional experiments have been performed with other drugs. Tablets of "Dramamine" (dimenhydrinate) of 50 mg concentration were crushed in a mortar and pestle, 8 tablets being granulated with 20 grams of a berry flavored floss sugar using isopropanol. The product was air dried overnight and spun using commercial cotton candy apparatus at a medium heat setting. The resultant material was packaged in various packaging material in 1 gram doses to test shelf life.

The experiment was repeated using 10 tablets of chlorpheniramine maleate, 4 mg/tablet, which were granulated with 20 grams of berry flavored floss sugar using isopropanol. The product was air dried overnight and spun using the commercial cotton candy apparatus at a medium heat setting. Doses of 1 gm each were packed in various pouches and sealed.

A sinus preparation consisting of acetaminophen, phenylpropanolamine and phenyltoloxamine, and marketed by H. L. Moore Co. under the brand name of "Sinu-Prep", was used, 8 tablets being crushed and granulated with 20 grams of berry flavored floss sugar using isopropanol. The granulation was dried overnight and spun utilizing commercial cotton candy apparatus. Pouches were filled and segregated for testing of longevity.

The result of this series of packaging tests revealed that a sucrose carrier produced an unstable product unless it could be stored in an impermeable hermetically sealed enclosure and was produced in a controlled low humidity environment.

The following additional tests were performed as set forth in Table IV, each following the same procedure of granulating, drying and spinning as described above, using a lime flavored floss sugar in the specified quantities, with small quantities of isopropanol, the product being spun at medium heat setting.

TABLE IV

| DRUG | QUANTITIES | |
|---|---|---|
| | DRUG | SUGAR |
| acetaminophen | 4 gm | 50 gm |
| phenylpropanolamine | 300 mg | 50 gm |

TABLE IV-continued

| DRUG | QUANTITIES | |
|---|---|---|
| | DRUG | SUGAR |
| chlorpheniramine maleate | 100 mg | 50 gm |
| aspirin* | 4 gm | 50 gm |

*Some degradation of the aspirin occurred as evidenced by excessive smoking and the characteristic odor of acetic acid. However, the fiber product had the characteristic taste of aspirin.

Various considerations enter into the choice of sugar, or sugars for use as the carrier for a given drug. As mentioned previously, the spin temperature must not exceed the deterioration temperature for the specific drug or active agent. Table V lists the melting points of various sugars, all of which can be spun into fibers.

TABLE V

| SUGAR | MELTING POINT | |
|---|---|---|
| | °C. | °F. |
| maltose R | 103 | 217.4 |
| fructose USP | 105 | 221.0 |
| sorbitol USP | 110 | 230.0 |
| dextrose USP | 146 | 294.8 |
| mannitol USP | 166 | 330.8 |
| sucrose USP | 186 | 366.8 |
| lactose R | 202 | 395.6 |

As a result of storage tests it has been discovered that sucrose is extremely susceptible to deterioration in the presence of moisture. However, it has been discovered that combining as little as 10% lactose with the sucrose produces a fibrous product after spinning that is significantly more stable. Apparently, the lactose has the physical ability of absorbing moisture without crumbling and functions as an active antidessicant. The lactose over time merely becomes softer and smoother. This becomes evident when pure lactose is spun and observed. Of course, pure lactose, with or without a separate sweetening agent, is an excellent carrier agent.

Adding lactose to the composition has another salutary effect. The spun fibers of sugar dissolve very rapidly in the mouth although unspun sugar dissolves rather slowly. As seen from Table V above, lactose has a much higher melting point and, therefore, spin temperature than sucrose. It has been discovered that by adding approximately 10% of a flavored lactose mixture to the sucrose and drug coprecipitate and spinning the resultant mixture at the sucrose temperature, the sucrose drug combination develops into fibers while the lactose, having a higher spin temperature, disperses uniformly throughout the fibrous mass as lactose granules. When administered orally the lactose dissolves more slowly in the mouth, taking perhaps one minute, and tends to eliminate any unpleasant aftertaste inherent in the drug. An example of a drug that would benefit from this treatment is acetaminophen.

Certain drugs or medicaments cannot be heated above their melting point without experiencing excessive deterioration. In such case a sugar should be chosen that can be spun effectively at a temperature below the melting point of the medicament, and the medicament should be able to disperse throughout the fibrous mass similar to the dispersal of the lactose throughout the sucrose mass as described above.

Of the various sugars, maltose and lactose when spun into fibers are much more stable than sucrose, that is, they are less affected by humidity. Consequently, it is presently preferred to include at least a small quantity of either lactose or maltose in any sugar carrier.

Experience to date has shown that sucrose and lactose can be spun with excellent results. Maltose because of its low melting point is ideal for certain drugs. However, it has been discovered that when maltose is spun using present equipment that is capable of rotating its spinnerette at 4000 R.P.M., the resultant fibers are much shorter than those obtained with sucrose or lactose. It is believed, however, that longer fibers of maltose can be obtained by using higher spinnerette speed.

Attempts to spin methyl cellulose with present equipment at 4000 R.P.M. have been met with gumming and charring of the material. It is believed that this problem also will be overcome by using higher spinnerette speed.

Because of the rapid release of a medicament when exposed to moisture, the instant product form is ideally suited for use in topical transdermal delivery of a medicament. For this purpose, the spun fibrous product can be compressed into thin sheets for production of wafers that can be combined with adhesive strips to produce bandage strips or patches. When, for example, the active agent or ingredient is an antibiotic or a clotting factor, it is released upon contact with a wound that emits blood or sera. On a burn, appropriate medicament will be released by tissue fluid. The invention is also applicable to patch technology in which sweat or skin moisture or even ambient moisture causes controlled release of a medicament or antigen from a fibrous layer held in contact with or in proximity to the skin.

In another area, certain pediatric suspension drugs, for example, amoxicillin, are provided to the pharmacists as a flavored powder in a sealed bottle. When the particular drug is to be dispensed, the pharmacist adds distilled water and shakes. However, the dissolution of the powder takes a long period of shaking wich is counterproductive and irritating to the pharmacist. When the present invention is employed and the drug is combined with a sugar carrier in fiber form, dissolution in distilled water is very rapid and occurs without shaking.

It is significant that drugs administered through the digestive tract are absorbed through the stomach and drain through the portal veins passing through the liver before entering into circulation. This reduces the drug concentration available in the blood stream and must be compensated by high dosage levels. This is avoided by the present invention when the fiber form of the medication is placed in the mouth either sublingually or buccally because it is absorbed, to a large degree, directly into the bloodstream bypassing the liver. This can be a significant advantage with drugs such as chlorpheniramine, nitroglycerin and methyltestosterone.

The present invention has a number of additional advantages. If medication in fiber form is placed on the tongue and taken with water, it behaves as if you were taking a solution, i.e., a liquid product. It eliminates the gagging phenomenon experienced by many individuals with pills or capsules. On the other hand if taken on the tongue without water, the dosage form manifests the combined characteristics of a buccal and oral dosage form.

Numerous examples have been mentioned above. However, the fundamental concept of transforming a drug or medicament into fiber form, wherein a fiber producing material acts somewhat as a scaffold to support the medicament for entry into solution almost instantaneously, can be applied to an extensive array of materials. In table VI below, the useful categories are set forth in the lefthand column in terms of pharmaceutical application, while the various forms which the fiber form product can take are specified in the righthand column using the following coding scheme:

A=fiber form for oral administration, including pre-dissolution in a liquid vehicle.

B=fiber form for incorporation in an adhesive bandage or patch.

C=fiber form for dissolution in H₂O or other liquid for topical application as a solution.

D=fiber form for bicameral or multicameral vials or pouches to replace lyophylized product.

TABLE VI

| CATEGORY | FORM |
|---|---|
| ACNE PREPARATIONS | A,C |
| ANALGESICS | A,B,C,D |
| ANTIPYRETICS | A,C,D |
| ANTACIDS | A |
| ANTIFLATULENTS | A |
| ANTHELMINTICS | A,D |
| ANTIANGINAL | A,D |
| ANTIANXIETY | A,B,D |
| ANTI-ARRYTHYMICS | A,D |
| ANTIARTHRITICS | A,B,C,D |
| ANTICOAGULANTS/THROMBOLYTICS | A,D |
| ANTICONVULSANTS/ANTIPARKINSON | A,D |
| ANTIDEPRESSANTS | A,D |
| ANTIDIARRHEAL/ELECTROLYTE SOLUTIONS | A,D |
| ANTIFUNGAL | A,B,C,D |
| ANTITRICHOMONAL | A,B,C,D |
| ANTIVIRAL AGENTS | A,B,C,D |
| ANTIGOUT | A,B,C,D |
| ANTIHISTAMINES | A,B,C,D |
| ANTIPRURITICS | A,B,C,D |
| ANTIHYPERTENSIVES | A,D |
| ANTIINFECTIVES (AMINOGLYCOSIDES, SULFONAMIDES, CEPHELOSPORINS, PENICILLINS, ERYTHROMYCINS, TETRACYCLINES) | |
| SYSTEMIC OF ABOVE | A,D |
| LOCAL OF ABOVE | A,B,C,D |
| ANTIMIGRAINES | A,B,D |
| ANTINAUSEANTS/ANTIEMETICS | A,B,D |
| ANTINEOPLASTICS | A,D |
| ANTIULCER | A,D |
| ANTIREFLUX | A,D |
| ANTISPASMODIC | A,D |
| BRONCHIAL DILATERS/ANTIASTHMATICS | A,D |
| CARDIAC AGENTS | A,D |
| CONTRACEPTIVES | A,D |
| HORMONALS | A,B,C,D |
| STEROIDS | A,B,C,D |
| COUGH/COLD REMEDIES | A,D |
| DIURETICS | A,D |
| HYPOGLYCEMICS | A,D |
| HYPOLIPIDEMICS | A,D |
| LAXATIVES | A |
| TRANQUILIZERS MAJOR & MINOR | A,B,D |
| MUSCLE RELAXANTS | A,D |
| OPTHALMIC PREPARATIONS | A,C,D |
| POTASSIUM SUPPLEMENTS | A,D |
| SEDATIVES AND HYPNOTICS | A,D |
| URINARY ANTINFECTIVES & OTHER URINARY AGENTS | A,D |
| VITAMINS AND MINERALS | A,D |

The foregoing tabulation is not intended to be exhaustive, but merely suggestive and illustrative of the vast area of application of the present invention.

It should be understood that reference herein to topical application of a material encompasses both those materials intended to act externally on the skin and those having the ability of being absorbed through the skin for transdermal systemic activity.

The term "medicament" and, therefore, "pharmaceutical" as used herein and in the appended claims means any drug, pharmaceutical, analytic reagent, or other ingredient having therapeutic activity or having utility in treating, testing or analyzing physiological conditions or body elements. It is intended to encompass ingredients that function as reagents in the analysis of substances that are indicative of physiological condition. For example, pyridoxal phosphate as used in LDH determination. Pyridoxal phosphate was prepared with lactose using IPA as a solvent substantially as described above with reference to the compounding of other materials with lactose. The composition was spun satisfactorily into a fibrous mass. It is advantageous in that it will dissolve in solution much more rapidly than existing tablet form of the reagent.

Having described the present invention with reference to the presently preferred embodiments thereof, it will be apparent to those skilled in the subject art that various changes and modifications can be incorporated without departing from the true spirit of the invention as defined in the appended claims.

What is claimed is:

1. A spun fibrous pharmaceutical composition comprising a mass of spun fibers of a material capable of being spun into fibers that are readily water-soluble and a medicament distributed on or incorporated in said fibrous mass.

2. A spun fibrous pharmaceutical composition according to claim 1, wherein said material is a sugar or a cellulosic material.

3. A spun fibrous pharmaceutical composition according to claim 2, wherein said material is a sugar.

4. A spun fibrous pharmaceutical composition according to claim 3, wherein said medicament is an analgesic.

5. A spun fibrous pharmaceutical composition according to claim 3, wherein said medicament is an antihistaminic labyrinthine function depressant.

6. A spun fibrous pharmaceutical composition according to claim 3, wherein said medicament is a decongestant.

7. A spun fibrous pharmaceutical composition according to claim 1, wherein said medicament is acetaminophen.

8. A spun fibrous pharmaceutical composition according to claim 1, wherein said medicament is diethylcarbamazine citrate.

9. A spun fibrous pharmaceutical composition according to claim 1, wherein said composition further comprises an adhesion promoter for promoting adhesion between said material and said medicament.

10. A spun fibrous pharmaceutical composition according to claim 9, wherein said adhesion promoter comprises polyvinylpyrrolidone.

11. A spun fibrous pharmaceutical composition according to claim 10, wherein said medicament comprises diethylcarbamazine citrate.

12. A spun fibrous pharmaceutical composition according to claim 3, wherein said sugar is selected from the group consisting of maltose, fructose, sorbitol, dextrose, mannitol, sucrose, lactose, and combinations thereof.

13. A spun fibrous pharmaceutical composition according to claim 12, wherein said mass of spun fibers is in the form of a compacted unit-dose body of said fibers where the fibers have retained their fibrous identity.

14. A spun fibrous pharmaceutical composition according to claim 1, wherein said mass of spun fibers is in the form of a compacted unit-dose body of said fibers where the fibers have retained their fibrous identity.

15. A spun fibrous pharmaceutical composition according to claim 3, wherein said sugar comprises at least 10% lactose and the remainder sucrose.

16. A spun fibrous pharmaceutical composition according to claim 12, wherein said medicament is of the type that is rapidly assimilated when in contact with the tissues of the oral cavity.

17. A pharmaceutical dosage unit comprising compacted spun fibers of a spinnable, readily water soluble material and an effective amount of a medicament.

18. A system for topical delivery of a medicament comprising a wafer containing a mass of fibers, and means for securing said wafer in contact with a dermal area to be treated, said mass of fibers, comprising a soluble fiber forming ingredient and a medicament where at least said fiber forming ingredient has been spun into fibers, and in said fiber form said ingredient has a solubility characteristic corresponding to that of spun sugar fibers in water.

19. A system according to claim 18, wherein said ingredient in fiber form is hydrophilic.

20. A system according to claim 19, wherein said ingredient is essentially lactose.

21. A system according to claim 18, wherein said medicament is a dermatotropic agent.

22. A system according to claim 18, wherein said medicament includes an antibiotic agent.

23. A system according to claim 18, wherein said medicament includes a corticosteroid.

24. A system according to claim 18, wherein said medicament is characterized by transdermal systemic activity.

25. A multicameral container for intravenous or intra muscular administration comprising a first compartment containing a pharmaceutically acceptable solvent, and a second compartment containing a spun fibrous pharmaceutical composition comprising a mass of spun fibers of a material capable of being spun into fibers that are readily water-soluble and a medicament distributed on or incorporated in said fibrous mass.

26. A multicameral container according to claim 25, wherein said material is a sugar selected from the group consisting of maltose, fructose, sorbitol, dextrose, mannitol, sucrose, lactose, and combinations thereof.

27. A multicameral container according to claim 26, wherein said mass of spun fibers is in the form of a compacted body of said fibers where the fibers have retained their fibrous identity.

28. A multicameral container according to claim 27, wherein said sugar comprises about 10% lactose and the remainder sucrose.

29. A spun fibrous pharmaceutical composition according to claim 29, wherein said material is methyl cellulose.

30. A spun fibrous pharmaceutical composition according to claim 29, wherein said medicament comprises dimenhydrinate.

31. A method for preparing a pharmaceutical dosage unit for delivering a medicament, comprising producing a mass of medicament bearing spun fibers by melt spinning a composition containing said medicament.

32. A method according to claim 31, wherein said medicament is combined with a melt spinnable compatible water soluble carrier agent to provide an intermediate product, and said intermediate product is converted to a mass of spun fibers by melt spinning product.

33. A method according to claim 32, wherein said carrier agent comprises a mixture of sucrose and lactose.

34. A method according to claim 33, wherein said lactose is combined with said sucrose in the ratio of about 1:9 by weight.

35. A method according to claim 32, wherein said medicament has a higher melting point than said carrier agent, and said melt spinning is carried out at a temperature lying between the melting points of said medicament and said carrier agent but less than the melting point of said medicament.

36. A method for preparing a rapidly dissoluble medicinal dosage unit for administering medication comprising in combination the steps of combining a medicament with a melt spinnable compatible carrier agent to provide an intermediate product, and producing a mass of medicament bearing fibers by melt spinning said intermediate product.

37. A method according to claim 36, wherein said carrier agent is a sugar having a spinning temperature below the degradation temperature of said medicament.

38. A method according to claim 37, wherein said intermediate product is produced by coating granules of said sugar with a slurry of said medicament where the vehicle for said slurry is not a solvent for said sugar.

39. A method according to claim 38, wherein said vehicle is isopropyl alcohol.

40. A method according to claim 39, wherein said granules of sugar are added to said slurry and the slurry coated granules are thereafter dried then spun to produce said fibers.

41. A method according to claim 40, wherein said slurry is produced by admixing acetaminophen with isopropyl alcohol to produce a 60-70% w/v solution of said medicament in said vehicle.

42. A method according to claim 40, wherein said slurry is produced by adding 2-3% by weight of polyvinylpyrrolidone to isopropyl alcohol and admixing the resulting solution with diethylcarbamazine citrate to obtain a slurry containing about 60% w/v of said medicament in said vehicle.

43. A method according to claim 36, wherein the spun fiber product resulting from said melt spinning of said intermediate product is compacted to produce a body whose enclosed volume is substantially less than the as-spun enclosed volume, and the compacted product is thereafter subdivided into dosage units.

44. A method according to claim 43, wherein said compaction step is performed to produce said body with an enclosed volume at least 30% less than said as-spun enclosed volume, said compaction step being limited to less than that compaction which would result in noticeable fracturing of said fibers.

45. A rapidly dissoluble spun fibrous medicinal dosage unit for administering medication orally, sublingually, or buccally, consisting essentially of a compacted mass of spun fibers of a carrier agent capable of being spun into fibers that are readily water-soluble which dissolve in the saliva of the mouth, said mass having an enclosed volume that is at least 30% less than the as-spun enclosed volume, said carrier agent being selected from the group consisting of sugars, sugar alcohols and mixtures thereof, and an effective amount of an orally, sublingually, or buccally effective medicament distributed within or coated on said spun carrier agent fibers.

46. A rapidly dissoluble medicinal dosage unit according to claim 45, wherein said medicament is acetaminophen.

47. A rapidly dissoluble medicinal dosage unit according to claim 45, wherein said medicament is diethylcarbamazine citrate.

48. A rapidly dissoluble medicinal dosage unit according to claim 45, wherein said fibers consist essentially of a compound containing said carrier agent and said medicament.

49. A rapidly dissoluble medicinal dosage unit according to claim 48, wherein said fibers are the product resulting from melt spinning of said compound.

50. A rapidly dissoluble medicinal dosage unit according to claim 49, wherein said medicament is acetaminophen.

51. A rapidly dissoluble medicinal dosage unit according to claim 49, wherein said medicament is diethylcarbamazine citrate.

52. A rapidly dissoluble medicinal dosage unit according to claim 48, wherein said compound consists essentially of said carrier agent, said medicament, and adducts selected from the group consisting of coloring agents, flavoring agents, and promoters of adhesion between said carrier agent and the other constituents.

53. A rapidly dissoluble medicinal dosage unit according to claim 52, wherein said adhesion promoter comprises polyvinylpyrrolidine.

54. A rapidly dissoluble medicinal dosage unit according to claim 53, wherein said medicament comprises diethylcarbamazine citrate.

55. A rapidly dissoluble medicinal dosage unit according to claim 45, wherein said mass of spun fibers is in the form of a tablet of compacted spun fibers where the fibers have retained their fibrous identity.

56. A rapidly dissoluble medicinal dosage unit according to claim 55, wherein said fibers consist essentially of a compound containing said carrier agent and said medicament.

57. A rapidly dissoluble medicinal dosage unit according to claim 56, wherein said fibers are the product resulting from melt spinning of said compound.

58. A rapidly dissoluble medicinal dosage unit according to claim 57, wherein said medicament is acetaminophen.

59. A rapidly dissoluble medicinal dosage unit according to claim 57, wherein said medicament is diethylcarbamazine citrate.

* * * * *

UNITED STATES PATENT AND TRADEMARK OFFICE
CERTIFICATE OF CORRECTION

PATENT NO. : 4,855,326

DATED : August 8, 1989

INVENTOR(S) : Richard C. Fuisz

It is certified that error appears in the above-identified patent and that said Letters Patent is hereby corrected as shown below:

Column 7, line 11, "flucose" should read --glucose--.
Column 8, line 21, "duplciate" should read --duplicate--.
Column 10, line 37, "wich" should read --which--.
Column 13, line 10, "pharmaceutical" should read --pharmaceutic--; line 55, "claim 29" should read --claim 1--.

Signed and Sealed this

Nineteenth Day of November, 1991

Attest:

HARRY F. MANBECK, JR.

*Attesting Officer*       *Commissioner of Patents and Trademarks*